(12) United States Patent
Takahashi et al.

(10) Patent No.: US 7,459,582 B2
(45) Date of Patent: *Dec. 2, 2008

(54) METHODS FOR PRODUCING NATEGLINIDE CRYSTALS

(75) Inventors: Daisuke Takahashi, Yokkaichi (JP); Seiichi Nishi, Yokkaichi (JP); Satoji Takahashi, Yokkaichi (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/686,073

(22) Filed: Mar. 14, 2007

(65) Prior Publication Data

US 2007/0167523 A1 Jul. 19, 2007

Related U.S. Application Data

(63) Continuation of application No. 10/418,105, filed on Apr. 18, 2003, now Pat. No. 7,208,622, which is a continuation of application No. PCT/JP01/09069, filed on Oct. 16, 2001.

(30) Foreign Application Priority Data

Oct. 18, 2000 (JP) .............................. 2000-317604

(51) Int. Cl.
    *C07C 229/00* (2006.01)
(52) U.S. Cl. ..................... 562/450; 562/444; 562/445
(58) Field of Classification Search ................ 562/444, 562/445, 450
    See application file for complete search history.

(56) References Cited

U.S. PATENT DOCUMENTS

| 4,816,484 A | 3/1989 | Toyoshima et al. |
| 5,463,116 A | 10/1995 | Sumikawa et al. |
| 6,844,008 B2 | 1/2005 | Yabuki et al. |
| 2003/0021843 A1 | 1/2003 | Makino et al. |
| 2003/0073729 A1 | 4/2003 | Kitahara et al. |
| 2003/0229249 A1 | 12/2003 | Sumikawa et al. |
| 2004/0014815 A1 | 1/2004 | Ninomiya et al. |
| 2004/0024219 A1 | 2/2004 | Sumikawa et al. |

FOREIGN PATENT DOCUMENTS

| EP | 0 196 222 | 10/1986 |
| EP | 0 526 171 | 2/1993 |
| JP | 04-015221 | 1/1992 |
| JP | 05-208943 | 8/1993 |
| JP | 07-017899 | 1/1995 |
| JP | 2508949 | 4/1996 |

*Primary Examiner*—Taylor Victor Oh
(74) *Attorney, Agent, or Firm*—Oblon, Spivak, McClelland, Maier & Neustadt, P.C.

(57) ABSTRACT

There is provided methods for producing nateglinide crystals, which comprises the steps of adding an acid(s) to a reaction mixture containing nateglinide to make it acidic, the reaction mixture being obtained by reacting trans-4-isopropylcyclohexylcarbonyl chloride with D-phenylalanine in a mixed solvent of ketone solvent and water in the presence of an alkali; and then adjusting the temperature of the mixture to 58° C. to 72° C. and the concentration of ketone solvent to more than 8 wt % and less than 22 wt % to conduct precipitation of nateglinide crystals. This producing method is the industrially beneficial methods for crystallization of nateglinide.

12 Claims, No Drawings

METHODS FOR PRODUCING NATEGLINIDE CRYSTALS

BACKGROUND OF THE INVENTION

The present invention relates to methods for producing N-(trans-4-isopropylcyclohexylcarbonyl)-D-phenylalanine (its general name is nateglinide and hereinafter referred to as nateglinide) that is useful as a therapeutic agent for diabetes. More specifically, it relates to industrially beneficial methods for crystallization of nateglinide.

It is known that nateglinide is useful as a therapeutic agent for diabetes because it effectively lowers blood glucose by oral administration (Japanese Patent Publication No. Hei 4-15221).

It is also known that nateglinide has crystal polymorphs and H-type crystals are useful among them (Japanese Patent No. 2508949).

On the other hand, in order to synthesize nateglinide, when trans-4-isopropylcyclohexylcarbonyl chloride and D-phenylalanine were reacted in a mixed solvent of ketone solvent and water, and H-type crystals of nateglinide were precipitated from the reaction mixture in accordance with the method described in Japanese Patent No. 2508949, the synthesized crystals were small and it took a long time to complete the separation by filtration when the filtering device available on the industrial scale was used. Therefore, it was found that the above-described method was not practical.

DISCLOSURE OF THE INVENTION

An object of the present invention is to provide methods for precipitating crystals of nateglinide that are industrially separable, using a reaction mixture containing nateglinide obtained by reacting trans-4-isopropylcyclohexylcarbonyl chloride with D-phenylalanine.

For the purpose of solving the above-described problems, the inventors have vigorously studied and found that the crystals that can be filtered out on the industrial scale can be separated out by using a mixed solvent of ketone solvent and water as a reaction solvent and neutralizing the reaction mixture, and then by selecting a range of the crystallization temperature and/or the mixture ratio of ketone solvent and water. The present invention has been completed on the basis of this finding.

Namely, the present invention provides the methods for producing nateglinide crystals, which comprises the steps of adding an acid(s) to a reaction mixture containing nateglinide to make it acidic, the reaction mixture being obtained by reacting trans-4-isopropylcyclohexylcarbonyl chloride with D-phenylalanine in a mixed solvent of ketone solvent and water in the presence of an alkali; and then adjusting the temperature of the mixture to 58° C. to 72° C. and the concentration of ketone solvent to more than 8 wt % and less than 22 wt % to conduct precipitation of nateglinide crystals.

The present invention also provides the nateglinide crystals obtained by the above-described producing method.

BEST MODE OF CARRYING OUT THE INVENTION

The reaction mixture containing nateglinide, which is an object of crystallization operation of the present invention, is prepared as follows. First, D-phenylalanine is dissolved in an alkali aqueous solution such as potassium hydroxide, and a ketone solvent(s) is added thereto. Then, trans-4-isopropylcyclohexylcarbonyl chloride is gradually added to conduct Schotten-Baumann reaction. After the reaction completes, the reaction mixture is made acidic by adding an acid(s).

D-phenylalanine used in the reaction is obtained by the following method. First, DL-phenylalanine obtained by the synthetic method is, for example, acetylized to synthesize N-acetyl-DL-phenylalanine. Then, N-acetyl-DL-phenylalanine is subjected to enzymatical acylase decomposition to obtain unreacted N-acetyl-D-phenylalanine. Further, the unreacted N-acetyl-D-phenylalanine is synthetically hydrolyzed to obtain the D-phenylalanine. It can be also obtained by the same method as that described above except that L-phenylalanine obtained by fermentation is racemized to synthesize DL-phenylalanine.

Trans-4-isopropylcyclohexylcarbonyl chloride used in the reaction is obtained by reacting trans-4-isopropylcyclohexan carboxylic acid which is a corresponding carboxylic acid with, for example, phosphorous chloride (Japanese Patent Un-examined Publication No. Hei 7-17899). It can be also obtained by an ordinary method for synthesizing an acid chloride from a carboxylic acid, such as the reaction with thionyl chloride.

The molar ratio of the reaction substances, that is, D-phenylalanine to trans-4-isopropylcyclohexylcarbonyl chloride in the above-described Schotten-Baumann reaction is preferably 0.5:1 to 2:1 and more preferably 0.9:1 to 1.5:1. The concentration of D-phenylalanine and trans-4-isopropylcyclohexylcarbonyl chloride in the reaction is preferably 2 wt % to 15 wt % in terms of the concentration of D-phenylalanine, if the molar ratio of each substance is within the above range.

The reaction temperature is preferably 20° C. or less in order to prevent the side reaction and more preferably 15° C. or less.

An alkali is preferably potassium hydroxide, but alkaline metals such as sodium hydroxide or other alkaline substance can be also used. Especially, it is preferable that pH of the mixture in the reaction should be kept in 10 to 13.9. Alkaline chemicals can be added to the reaction mixture so that the pH can be kept within the above range.

Acetone, methylethylketone and the like can be used as the ketone solvent used in the above-described Schotten-Baumann reaction and the crystallization operation from the reaction mixture. The solvent in the reaction and that in the crystallization should be the same because the solvent is collected after crystallization and separation. Therefore, acetone is most preferable in view of its yield in the reaction and processing.

Further, the ratio of water to ketone solvent (weight ratio) should be 10:1 to 0.5:1 and preferably 6:1 to 1:1 in respect of its yield. The ketone solvent(s) in the present reaction is usually essential to proceed the reaction. However, a large quantity of acetone in the reaction causes high proportion of by-product. Therefore, it is preferable that an amount of the ketone solvent should be relatively small in the reaction.

The intended nateglinide crystals can be obtained by crystallizing the reaction mixture that is made acidic by adding acids after the completion of the above-described Schotten-Baumann reaction. The acids added to the reaction mixture are any of those which make the reaction mixture acidic. Hydrochloric acid, sulfuric acid and the like can be used, and hydrochloric acid is preferable. The pH of the crystallization mixture should be acidic and preferably 2 or less and more preferably 1.5 or less.

The concentration of the ketone solvent in the obtained reaction mixture needs to be controlled to separate out the intended crystals of the present invention, that is, the easily filtered crystals. Because the acid(s) is added to the reaction mixture as described above, the ketone solvent usually needs to be added to the reaction mixture in order to adjust the crystallization mixture to the intended concentration of the ketone solvent. Both ways are acceptable that the acid(s) is added to the reaction mixture and that the reaction mixture is added to the acid(s). Further, both are acceptable that the ketone solvent is added after the mixture is made acidic by the acid(s) and that the acid(s) can be added after the ketone solvent is added.

From the above reasons, the ratio of the ketone solvent to water in the reaction is usually lower than that of the all ketone solvent needed in the crystallization operation of the present invention. Therefore, when the present invention is carried out, the concentration of the ketone solvent is often preferably adjusted by adding further ketone solvent after the reaction mixture is neutralized.

The crystals are precipitated by the crystallization operation in that the concentration of the ketone solvent is, if necessary, adjusted to more than 8 wt % and less than 22 wt % and preferably 12 wt % to 16 wt %, and that the range of the crystallization temperature is 58° C. to 72° C. A seed crystal may be added after the crystallization temperature is set to the intended temperature. Crystallization may be conducted by stirring or by still standing. The crystallization by stirring makes procedures followed by the crystallization easier.

In the present invention, when the concentration of the ketone solvent is more than 8 wt % and less than 22 wt %, the precipitated crystals are easily filtered out and the filtration can be completed in a short time on the industrial scale.

In addition, when the crystallization temperature is 58° C. to 72° C., the separated crystals are easily filtered out and the filtration can be completed in a short time on the industrial scale.

It is most preferable that the reaction is conducted in such that the concentration of the ketone solvent in the reaction mixture is 10 wt % to 20 wt % and then a ketone solvent is added after neutralization of the reaction mixture so that the concentration of the ketone solvent in the mixture is 12 wt % to 16 wt %.

The period of time for crystallization (crystal maturation time) ranges from 10 minutes to 24 hours and preferably from 30 minutes to about 3 hours.

According to the crystallization at the temperature and in the ratio of the ketone solvent defined by the present invention, the crystals are precipitated, in which bundles are formed by many needle crystals, as well as the conventional crystals. However, the crystals of the present invention can be obtained in the form of more grown, precipitated and easily filterable ones having an average long axis (mean long diameter) of 1 mm to 5 mm and an average short axis (Mean short diameter) of 0.1 mm to 0.5 mm.

The formed crystals can be precipitated from a mother liquor by a centrifuge and the like to isolate them.

The crystals obtained in the present invention can be filtered out in a short time, especially by a separator used on the industrial scale. Further, the less mother liquor adheres to the crystals after filtration and therefore, the crystals having highly purified can be efficiently obtained.

The nateglinide crystals obtained by the above-described method can be recrystallized to further purify them in accordance with the methods, for example, of Japanese Patent No. 2508949 when they are used as a basic ingredient of pharmaceutical products.

The following Examples and Comparative Examples will further illustrate the present invention, which by no means limit the invention.

EXAMPLE 1

24.36 g of D-phenylalanine was dissolved in 155 g of water and 93.9 g of 10 wt % KOH aqueous solution. 70.4 g of acetone was added thereto and then 22.77 g of trans-4-isopropylcyclohexylcarbonyl chloride was further added to the solution in 1.5 hours. In the meanwhile, 71.8 g of 10 wt % KOH aqueous solution was added to the reaction mixture in order to maintain pH of the mixture of 13.7 to 14.3 and the reaction mixture was cooled down to maintain a constant temperature of 15° C. or less. Thus, 438.2 g of the acylated reaction mixture containing nateglinide was obtained.

12.6 ml of water and 11.0 g of acetone were added to a part (202.5 g) of the acylated reaction mixture in order to adjust the concentration of the mixture. A mixture of 12.0 g of 35 wt % HCl aqueous solution and 60.2 g of water was added thereto in 1.5 hours. The obtained crystallization slurry (acetone concentration: 14.6 wt %) was stirred at 66° C. overnight. As the slurry was precipitated, stirring was stopped and the precipitated crystals were separated and observed under a microscope. The crystals were obtained in the form of the bundles of the needle crystals. The sizes of those bundled crystals were in average about 0.2 mm in width and about 2 mm in length. When analyzed the obtained crystals by a powder X-ray diffractometer, the existence of diffraction peaks of 8.1°, 13.1°, 19.6° and 19.9° (2 θ) was identified and therefore the crystals were confirmed as H-type crystals.

COMPARATIVE EXAMPLE 1

The acylated reaction mixture obtained by the same procedure as that of Example 1 was stirred and crystallized at 45° C. in 8 wt % acetone concentration overnight. The obtained slurry did not have sedimental property. As the result of observing it under a microscope, the needle crystals were bundled but each needle crystal was smaller and its degree of bundling was lower than that of Example 1. The sizes of those bundled crystals were in average about 0.02 mm in width and about 0.1 mm in length.

COMPARATIVE EXAMPLE 2

The acylated reaction mixture obtained by the same procedure as that of Example 1 was adjusted to 22 wt % acetone concentration and stirred at 73° C. overnight. The resulting mixture was in the form of oil and not crystallized.

EXAMPLES 2 to 11 AND COMPARATIVE EXAMPLES 3 TO 13

The following slurries of Examples 2 to 11 and Comparative Examples 3 to 13 were obtained by the same reaction and the crystallization operation as those of Example 1 except that the acetone concentration and the crystallization temperature were changed. The precipitation condition of the crystals was investigated and the crystals were observed microscopically.

EXAMPLE 12

(Evaluation of Separating Properties 1: Acetone Concentration 14%, Crystallization Temperature 65° C.)

38.14 kg of D-phenylalanine, 40.1 kg of trans-4-isopropylcyclohexylcarbonyl chloride, and corresponding amounts of water, 10 wt % KOH aqueous solution and acetone were used in the same ratio as that of Example 1 to conduct acylation reaction in a crystallization can having 2 KL capacity. As a result, 728 kg of the acylated reaction mixture containing nateglinide was obtained. The obtained reaction mixture was added to a mixture of 249 L of water and 45.1 kg of 35 wt % HCl aqueous solution. 62 L of acetone was further added thereto to adjust a total acetone concentration to 14.4 wt %. The mixture was stirred and aged at 63° C. to 65° C. for 17 hours and then cooled down to 30° C. As the result of observing the obtained slurry under a microscope, the needle crystals agglutinated. A whole amount of about 1200 L of slurry, about 400 L each time, was separated into the solids and the liquids in three times by a centrifugal precipitator of which basket diameter is 36 inches. After solid-liquid separation of the slurry, each of the crystals in the precipitator was washed with 150 L of water. It took about 16 minutes in average until the filtrate was not produced after pouring the rinse water.

104.9 kg of the total amount of the wet crystals was obtained by the three-time separations. Its average drying loss at 105° C. for 2 hours was 35.9%.

COMPARATIVE EXAMPLE 14

(Evaluation of separating properties 2: acetone concentration 8 wt %, crystallization temperature 45° C.)

727 kg of the acylated reaction mixture containing nateglinide was obtained as a result of acylation of D-phenylalanine on the same scale by using the same equipment as that of Example 12. The mixture was adjusted to acetone concentration 8 wt % and stirred and aged at 45° C. for 17 hours and then cooled down to 30° C. As the result of observing the obtained slurry under a microscope, the needle crystals were produced but hardly agglutinated.

A whole amount of about 1200 L of slurry, about 300 L each time, was separated into the solids and the liquids in four times by the centrifugal precipitator. Each of the crystals obtained by separation was washed with 110 L of water. It took about 30 minutes in average until the filtrate was not produced after pouring the washing water.

162.3 kg of the total amount of the wet crystals was obtained by the four-time separations. Its average drying loss was 60.8%.

All of the results of Examples 2 to 11 and Comparative Examples 3 to 13 are shown in Table 1.

TABLE 1

| | Acetone concentration (wt %) | Crystallization temperature (° C.) | Precipitation | Observation under a microscope |
|---|---|---|---|---|
| Comparative Example 3 | 8 | 45 | No | Same as Comp. Exam. 1 |
| Comparative Example 4 | 8 | 55 | No | Same as Comp. Exam. 1 |
| Example 2 | 10 | 70 | Yes | Same as Exam. 1 |
| Comparative Example 5 | 11.5 | 57 | No | Same as Comp. Exam. 1 |
| Example 3 | 12 | 65 | Yes | Same as Exam. 1 |
| Example 4 | 12 | 70 | Yes | Same as Exam. 1 |
| Comparative Example 6 | 13 | 55 | No | Same as Comp. Exam. 1 |
| Example 5 | 13 | 60 | Yes | Same as Exam. 1 |
| Comparative Example 7 | 13.5 | 73 | (in the form of oil) | (in the form of oil) |
| Comparative Example 8 | 14 | 50 | No | Same as Comp. Exam. 1 |

TABLE 1-continued

| | Acetone concentration (wt %) | Crystallization temperature (° C.) | Precipitation | Observation under a microscope |
|---|---|---|---|---|
| Example 6 | 14 | 72 | Yes | Same as Exam. 1 |
| Comparative Example 9 | 14.5 | 73 | (in the form of oil) | (in the form of oil) |
| Comparative Example 10 | 14.5 | 78 | (in the form of oil) | (in the form of oil) |
| Example 7 | 14.6 | 66 | Yes | Same as Exam. 1 |
| Example 8 | 15 | 60 | Yes | Same as Exam. 1 |
| Example 9 | 16 | 65 | Yes | Same as Exam. 1 |
| Example 10 | 16 | 67 | Yes | Same as Exam. 1 |
| Comparative Example 11 | 20 | 50 | No | Same as Comp. Exam. 1 |
| Example 11 | 20 | 58 | Yes | Same as Exam. 1 |
| Comparative Example 12 | 22 | 65 | (in the form of oil) | (in the form of oil) |
| Comparative Example 13 | 22 | 73 | (in the form of oil) | (in the form of oil) |

It is obvious from the results of the above-described Examples and Comparative Examples that, under the crystallization conditions in the methods for producing crystals of the present invention, easily filterable crystals are precipitated and the nateglinide crystals can be efficiently isolated from the reaction mixture when they are produced on the industrial scale.

What is claimed is:

1. A method for producing nateglinide crystals, which comprises:
    (a) mixing hydrochloric acid and, optionally, one or more acids with a first reaction mixture, said first reaction mixture comprising nateglinide, to obtain a second reaction mixture which is acidic, wherein said first reaction mixture is obtained by reacting trans-4-isopropylcyclohexylcarbonyl chloride with D-phenylalanine in a mixed solvent comprising acetone and water in the presence of potassium hydroxide;
    (b) adjusting the temperature of said second reaction mixture to 63° C. to 65° C. and the concentration of acetone to more than 8 wt % and less than 22 wt %, maintaining the second reaction mixture at 63° C. to 65° C., and cooling the second reaction mixture to effect precipitation of nateglinide crystals; and
    (c) isolating the nateglinide crystals.

2. The method according to claim 1, wherein the concentration of said acetone is adjusted by adding acetone to said first reaction mixture.

3. The method according to claim 1, wherein the concentration of said acetone is adjusted by adding acetone to said second reaction mixture.

4. The method according to claim 1, the concentration of said acetone adjusted to 12 wt % to 16 wt %.

5. The method according to claim 1, wherein said crystals are H-type crystals.

6. The method according to claim 1, wherein the concentration of said acetone is adjusted to 14.4 wt %.

7. The method according to claim 1, wherein said cooling is to 30° C.

8. The method according to claim 1, wherein said maintaining is for 17 hours.

9. The method according to claim 1, wherein one or more acids is at least sulfuric acid, and mixtures thereof.

10. The method according to claim 1, wherein said second reaction mixture has a pH of less than 2.

11. The method according to claim 1, wherein said mixing is carried out by adding said one or more acids to said first reaction mixture.

12. The method according to claim 1, wherein said mixing is carried out by adding said first reaction mixture to said one or more acids.

* * * * *